United States Patent
MacDonald

(10) Patent No.: US 9,710,221 B2
(45) Date of Patent: Jul. 18, 2017

(54) INTELLIGENT SAFER MUSIC SYSTEM FOR AN OPERATING ROOM

(71) Applicant: Alistair James MacDonald, Missoula, MT (US)

(72) Inventor: Alistair James MacDonald, Missoula, MT (US)

( * ) Notice: Subject to any disclaimer, the term of this patent is extended or adjusted under 35 U.S.C. 154(b) by 0 days.

(21) Appl. No.: 14/958,724

(22) Filed: Dec. 3, 2015

(65) Prior Publication Data

US 2016/0179460 A1    Jun. 23, 2016

Related U.S. Application Data

(60) Provisional application No. 62/095,961, filed on Dec. 23, 2014.

(51) Int. Cl.
| | | |
|---|---|---|
| *G06F 3/16* | (2006.01) | |
| *A61B 5/0205* | (2006.01) | |
| *H04R 3/00* | (2006.01) | |

(52) U.S. Cl.
CPC ............ *G06F 3/165* (2013.01); *A61B 5/0205* (2013.01); *H04R 3/00* (2013.01); *A61B 2503/12* (2013.01); *H04R 2430/01* (2013.01)

(58) Field of Classification Search
CPC ....... H04R 3/00; H04R 2430/01; G06F 3/165; A61B 5/0205; A61B 2503/12; H03G 5/00; H03G 5/16
USPC .................................................. 381/104, 107
See application file for complete search history.

(56) References Cited

U.S. PATENT DOCUMENTS

| | | | |
|---|---|---|---|
| 4,107,464 A | 8/1978 | Lynch et al. | |
| 7,224,282 B2 * | 5/2007 | Terauchi | A61B 5/00 340/4.13 |
| 8,620,682 B2 | 12/2013 | Bechtel et al. | |
| 2005/0126370 A1 * | 6/2005 | Takai | A63B 24/0003 84/636 |
| 2008/0153417 A1 | 6/2008 | Bhakta et al. | |
| 2009/0196437 A1 * | 8/2009 | Yamamoto | H03F 1/305 381/107 |
| 2014/0254831 A1 * | 9/2014 | Patton | H03G 3/20 381/107 |
| 2016/0022218 A1 * | 1/2016 | Hayes | A61G 7/005 600/301 |

* cited by examiner

*Primary Examiner* — Vivian Chin
*Assistant Examiner* — Jason R Kurr
(74) *Attorney, Agent, or Firm* — Seed IP Law Group LLP

(57) ABSTRACT

An integrated and reactive music control system designed for silencing music in an operating room during critical events. The preferred system contains a music input, a hardware interface to integrate real-time patient physiologic data, a software application to process the data, a user interface, and a music output, any portion or all of which may be hardwired or wireless. Through the user interface, medical personnel may adjust pre-set limits on physiologic parameters that indicate abnormality or risk to a particular patient. To reduce ambient noise pollution and permit communication and concentration of the surgical team, volume is reduced as a patient's condition deteriorates. Resulting in additional safety to patients in the operating room, the cessation of music may capture the attention of health care professionals who suffer from alarm desensitization. The system's integration includes an anesthesia monitor, but may extend to include a hospital data server and EMR systems.

17 Claims, 10 Drawing Sheets

INTELLIGENT SAFER MUSIC SYSTEM FOR AN OPERATING ROOM

BACKGROUND

Technical Field of

This disclosure relates to music systems and especially to music systems used in medical facilities such as surgical operating rooms or hospitals.

Description of the Related Art

Years of medical research, innovation and progress, have resulted in medical indicators for assessing patient risk. When a patient undergoes surgery, professional standards mandate that the patient be connected to monitors that continuously measure heart rate, blood pressure, arterial oxygen saturation, as well as other physiologic parameters. While these vital signs are visually displayed on a monitor screen, readings outside of normal, pre-defined ranges also trigger audio alarms in the monitoring equipment in order to alert medical personnel. However, with conservative parameters these alarm tones are relatively common and sometimes go unnoticed due to desensitization, a syndrome known as "alarm fatigue". In the operating room, these alarms may be inaudible at times due to excessive levels of noise and therefore may go unnoticed by health care professionals.

In a recent study, Dr. Schlesinger et at assessed the ability of resident anesthesiologists to detect changes in pulse oximetry in a noisy operating room environment. Currently, an anesthesia provider must battle with high levels of ambient noise including powered surgical instruments, suction, forced air warmers, conversation, and background music to try to detect the sounds of the patient's heart rate, oxygen saturation and alarm tones. It should be noted that the operating room setting has notoriously poor room acoustics caused by sound-reflective floor, wall, and ceiling surfaces designed for easy sanitization. Specific challenges are presented by the use of stereo systems, with which most operating rooms are equipped. In the era of iPods and Pandora, it is common for a surgeon to play music of his or her choice during surgery. Because of poor acoustics in an operating room and competing ambient noise, music is sometimes played at high decibel levels so that it can be heard. This poses a risk for important warning tones, pitches, and alarms from the anesthesia monitor becoming inaudible.

The auditory challenges faced by anesthesiologists were discussed in the 2014 article by Jonathan D. Katz, M.D. titled *Noise in the Operating Room* which appeared in the journal, *Anesthesiology*. Attached hereto as Appendix A and incorporated by this reference as though fully set forth herein. Katz highlighted some of the issues of noise pollution and alarm fatigue in the operating room setting. A medical team's ability to recognize a vital sign alarm and provide a timely response to that alarm can be the difference between life and death for a patient. Noise pollution compromises the attention of health care professionals and compromises patient safety in the operating room, putting patients at risk. Conservatively programmed monitor alarms become overly familiar to health care professionals, resulting in desensitization and alarm fatigue. Sometimes alarms are simply drowned out by the other sounds in the operating room that can exceed 130 dBA. The music commonly played in the operating room setting can contribute heavily to noise pollution—up to 87 dBA—and reduce the ease and accuracy of performing tasks. See Katz article, http://www.cspsteam.org/noiseanddistraction/NoiseintheOperatingRoom35.pdf. In the operating room, speakers are typically placed far away from patients and work instruments and may not be within ready reach of medical professionals during surgery, particularly when an emergency occurs.

In health care facilities, advances in technology of medical monitors, hospital servers, and electronic health records makes communication between these systems the norm. Live data readings are fed into a patient's medical record during surgery, constantly reporting on vital signs readings and changes. See article title Making Connections attached hereto as Appendix B and incorporated by this reference. Medical monitors can be grouped into three basic categories based on how data is sent from each type of device: episodic, continuous stand-alone, and continuous networked. Other categories and configurations may be possible but these three represent the most common. Additionally, it is possible that some devices may fall into overlapping categories.

In the surgical operating room setting, anesthesia monitors may fall into either continuous stand-alone or continuous networked categories. Because they may be tied to a single location, continuous stand-alone devices may be hard wired to communicate with the hospital network via a wireless or LAN connection. Continuous networked devices, such as physiologic monitoring systems and networked infusion pumps, monitor and/or treat a single patient over an extended period and are connected to a central server supplied by the device vendor. Due to the direct connection, no additional components are required in order for the continuous networked devices to collect and translate data directly to the host server via the hospital network. Continuous stand alone devices, such as a ventilator, are used to continuously monitor and/or treat a single patient over an extended period, but are typically not networked to any vendor-supplied central server (also referred to as a gateway). With the exception of anesthesia and intensive care unit monitors, most vital sign monitors are episodic devices. Episodic devices obtain a single set of measurements such as noninvasive blood pressure, oxygen saturation, temperature, and pulse rate from a patient at any given time. In other words, episodic devices provide spot check readings for a patient at the point of care. Episodic devices are coupled via wired connection with a point of care (POC) component which communicates readings from the device via a wireless network.

While careful attention has been employed in advancing technology for informational and medical equipment, music players for operating rooms have not been provided such attention. In the separate marketplace, music players have evolved. Now, an entire library of music can be housed on a very small device or accessed via a network connection. Internet access and Wi-Fi connectivity prominent in hospitals makes Internet radio or cloud-based libraries immediately accessible. In most instances, a music file is accessed and played through a speaker or speakers. Wired speaker connections like RCA connectors or 3.5 mm cords have been around for decades, but Bluetooth® and wireless speakers are becoming very common. New wireless speaker adapters are making it possible for any speaker system to be a Bluetooth® compatible speaker system which can be connected wirelessly to a music player over long or short ranges. The ready accessibility to music permits surgeons to play any genre of music at any time. Technological convenience has opened the door to allow ease of access to music in the operating room, yet music players are still not crossing over to communicate with the technologically advanced medical monitors and equipment.

BRIEF SUMMARY

A control device for an operating room audio system is integrated with patient vital sign monitors with an objective of reducing one of the contributors to the high levels of noise in an operating room, specifically the ambient music playing in the background. The noise reduction will allow doctors to recognize and be alerted to the alarms on the monitors signaling patient distress. In the preferred implementation, an audio system for use in an operating room comprises an audio input, a hardware interface receiving continuous real-time patient data, a software application to process patient data, a user interface for the software application, and an audio output to convey sound to a speaker system. Conveyance of music is contingent upon vital signs registering within normal parameters set by a medical professional. Music volume will be restricted if the vital sign readings indicate the patient is tending toward or has entered a zone of health risk as predetermined by the physician's vital sign parameter settings. The restriction of volume will create a quieter environment to facilitate communication and concentration of the surgical team during critical times.

The present disclosure provides an operating room stereo system that integrates with the anesthesia monitor. As an example of its function, the new stereo system will not play music or will mute music if the pulse oximeter reading falls below a value of 80%. Additional vital sign thresholds and volume responses may be included. The primary benefit of the system is facilitating concentration and communication of the surgical team at important moments. A secondary benefit may be that the cessation of music may serve to capture the attention of an operating room team that has become desensitized to alarm tones. For truly concerning alarms such as critically low blood pressure, heart rate, or oxygen saturation, adding the redundancy of music volume reduction to the existing monitor alarms provides an extra level of safety. Allowing music only when the patients vital signs are in an acceptable range is an important and novel evolution in patient safety.

An alternative implementation of the present disclosure presents a bridging apparatus for use in an operating room, the apparatus having at least one input to receive information from a patient monitor and further having an output to convey commands to control an audio system. The provided bridge hardware component with at least one port will provide connectivity to an anesthesia monitor or similar medical monitoring device, especially one that moves between patients. The bridge is connected to the monitoring device via a wired connection and travels with the device. The bridge optionally connects to a server via Ethernet or Wi-Fi connection (using the IEEE 802.11 a/b/g standard). The bridge can also be fixed within a room (e.g., mounted on the wall) and can provide connectivity to any bedside device. In hospital rooms such a device could be used to silence music when a patient needs medical assistance. Advanced or high-end models will permit options for all input and output to be made wirelessly.

In another implementation, a free standing external music control unit quiets, mutes, silences, pauses, or powers off ambient music in an operating room. Herein, quiet, mute, silence, pause, or power off may be collectively referred to as "mute". The music control unit comprises at least one input to receive information from a patient monitor and further comprises an audio output control.

In yet another implementation, an alarm system for an operating room mutes music as part of the monitor's integrated alarm system which is controlled by on-board software. Such an integrated alarm system presented in this implementation and the following implementation may be less desirable in the field because they are more likely to require Class II medical device vetting by the FDA.

In a further implementation, a smart music system implementation may integrate silencing functions through interaction with the anesthesia monitor or electronic medical record (EMR). This model or other models interfacing with an EMR may do so with a HL7 universal format for patient monitor data. See, Appendix C attached hereto also located at http://www.hl7.org/implement/standards/product_brief.cfm?product_id=6 incorporated by this reference. The HL7 standard allows interoperability of medical device vendors to retain meaning of data. Presently, the monitor company Nihon Kohden can connect to the systems listed at http://www.nkusa.com/files/pdf/CGS9002PlatinumHL7BidirectionalInterface.pdf and also attached hereto as Appendix D and incorporated by this reference. The music system, if not hardwired directly to the monitor in the room, could access the same data for that particular monitor through the hospital or vendor network and server. Data also could be accessed through an EMR system that feeds into a hospital network. Under present networking speed conditions this option is less desirable as it is likely to result in a slight delay (several seconds) but when implemented in improved networks of the future, this implementation may become more practical.

In accordance with another aspect of the present disclosure, a device for controlling volume of a music source in a medical operating room environment in response to a patient's medical condition as determined by existing monitoring equipment is provided. The device includes a first input coupled to the patient monitoring equipment and structured to receive a patient condition signal from the patient monitoring equipment, an output coupled to the music source, and a signal processor coupled to the first input and to the output and structured to receive the patient condition signal and to generate a music volume control signal on the output to adjust the volume of the music source in response to the patient condition signal in which the volume is reduced but not muted in response to the patient condition signal being in a first range and muting the volume of the music source in response to the patient condition signal being within a second range.

In accordance with a further aspect of the present disclosure, the first and second ranges are mutually exclusive.

In accordance with yet another aspect of the present disclosure, a system for providing music to a music speaker system in response to patient condition signals from patient monitoring equipment is provided. The system has a music player that includes a first input coupled to the patient monitoring equipment and structured to receive the patient condition signals from the patient monitoring equipment, an output coupled to the music speakers, an audio system having an input terminal, an output terminal coupled to the output of the music player, and structured to output an audio signal to the music speaker system, and a signal processor having an input terminal coupled to the first input to receive the patient condition signals and an output terminal coupled to the input terminal of the audio system, the processor structured to generate a music volume control signal on the output terminal to the audio system to adjust a volume level of the audio signal in response to the patient condition signals in which the volume level of the audio signal is reduced but not muted in response to the patient condition signals being within a first range and muting the volume level of the audio signal in response to the patient condition signal being within a second range.

In accordance with still yet another aspect of the present disclosure, a system for controlling music volume in a medical setting in response to a patient's condition is provided. The system includes monitoring equipment adapted to monitor the patient's condition and to generate patient condition signals, an electronic patient record system adapted to store and retrieve the patient's medical records, the electronic patient record system coupled to the monitoring equipment to receive the patient condition signals and update the patient's medical records, a music source capable of generating audio music signals, a music output system capable of receiving the audio music signals and outputting audible music in response to the audio music signals, and a signal processor coupled to the monitoring equipment to receive the patient condition signals, the signal processor further coupled between the music source and the music output system, the processor structured to receive the audio music signals from the music source and to generate a music volume control signal to the music output system to adjust a volume of the audible music in response to the patient condition signals in which the volume of the audible music is reduced but not muted in response to the patient condition signals being within a first range and muting the volume of the audible music in response to the patient condition signals being within a second range.

With the omnipresence of music in today's operating rooms, integration of music systems with the anesthesia monitor is advantageous. For example, if the music suddenly stops because the patient's oxygen saturation has fallen below 80%, it may capture the attention of everybody in the room more than the quietly descending pitch of the oximeter. The abrupt stopping of music might be followed by cessation of unnecessary conversation, focusing the entire operating room team on the safety of the patient and reducing the odds of an adverse outcome. Anesthesia providers responsible for monitoring the patient would struggle less to hear important tones and alarms over high levels of unnecessary ambient noise.

The patient-centered audio system automatically mutes music if patient vital signs become abnormal or unstable. The instructions for automatic muting are conveyed by the software application receiving vital sign information from a patient monitor. Programming allows a medical professional to set vital sign parameter thresholds according to practice or hospital standards based on the particular patient's medical condition and the planned surgical procedure. The software will process and analyze the information conveyed by the patient monitor according to the thresholds set by the medical professionals. Vital sign readings which exceed parameters or indicate aberrations or abnormalities will result in output instructions to mute ambient music.

The audio input will typically be a personal computing device such as an tablet, computer, iPod, mobile phone, Mp3 Player, or the like, capable of receiving music information like radio or electronic files and transmitting the music to a speaker through an amplifier when provided. The hardware interface may be retrofitted to existing monitoring equipment through the interfacing port, integrated into monitors at manufacturing, or may be a free standing device external of other operating room equipment. In progressive implementations, the hardware receiving patient data may be as simple as a device interacting with a patient such as by contact, collecting and transmitting data to a mobile processor, tablet, processor, or directly into an electronic medical record file. The software component may be a stand-alone application or may be presented in conjunction with additional software. The software application will have settings for vital sign parameters that may be tailored by medical professionals according to patient needs. Surpassing a certain single, parameter such as oxygen saturation will be enough to trigger the system to mute music. However, any combination of various vital sign readings that indicate patient risk will be programmed to reduce or eliminate music volume by the music output control.

The preferred audio or music output will be connected via wired connection to a downstream amplifier (if used) and speakers. Some audio system configurations are a single unit of amplifier and speakers. Other audio systems are also integrated with the music input. The outgoing control signal from the bridge is configured in various manners to communicate with the applicable audio system. The outgoing control will reduce the decibels to a low level or mute the sound in the operating room. In one implementation, a switch interrupts the signal from the hardware and software interface receiving transmissions from the music input which permits music to be transmitted to the speakers and emitted into the operating room. This interruption is like a negative control on the audio transmission and only permits audio on or off without descending decibel options. For more sophisticated, integrated devices, a positive control will only allow music when the patient's vital signs are within safe ranges. Other positive controls such as linear reduction or drastically descending options for the decibel volume output from a device are included in alternative models.

Some implementations of the present disclosure will provide software-only solutions that can be installed on any off-the-shelf hardware (e.g., existing iPods, PCs, tablets, or workstations) and provides connectivity to monitor devices. The integrated music and alarm system may be applied to episodic devices as well as static or semi-static medical monitors. Hardware such as a PC platform can be provided by the hospital or with the system. A PC platform is attached to the medical monitor via a wired or other connection and is transported along with it. Similar to the bridging device, any hardware may communicate with a server by wired connection or wirelessly via the hospital or facility network. A wired PC platform connects to the medical device via the vendor-supplied cables. The hardware may be configured to communicate with the server accordingly.

Ideally, a single device will be provided for a single surgical operating room. Such a fixed location will make a hardwired connection convenient and a hardwired connection will increase speed and reliability of data transfer and response of the present disclosure. A hardwired connection will require a device specific cable and device specific cables may complicate connectivity options. Alternative implementations will allow wireless communication between components of the present disclosure. Convenience in connectivity, sterility, and mobility will need to be weighed against speed and reliability of consistent communication. Device enhancements such as LED indicator lights may be incorporated to assist with visual cues of signal strength or device connectivity.

The foregoing has outlined, in general, the physical aspects of the disclosure and is to serve as an aid to better understanding the more complete detailed description which is to follow. In reference to such, there is to be a clear understanding that the present disclosure is not limited to the method or detail of construction, fabrication, material, or application of use described and illustrated herein. Any other variation of fabrication, use, or application should be considered apparent as an alternative implementation of the present disclosure.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures or components or both associated with software, source code, data flow and control flow have not been shown or described in order to avoid unnecessarily obscuring descriptions of the implementations.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one implementation" or "an implementation" means that a particular feature, structure, or characteristic described in connection with the implementation is included in at least one implementation. Thus, the appearance of the phrases "in one implementation" or "in an implementation" in various places throughout the specification are not necessarily all referring to the same implementation. Furthermore, the particular features, structures, or characteristics may be combined in any suitable manner in one or more implementations.

Figure 1:
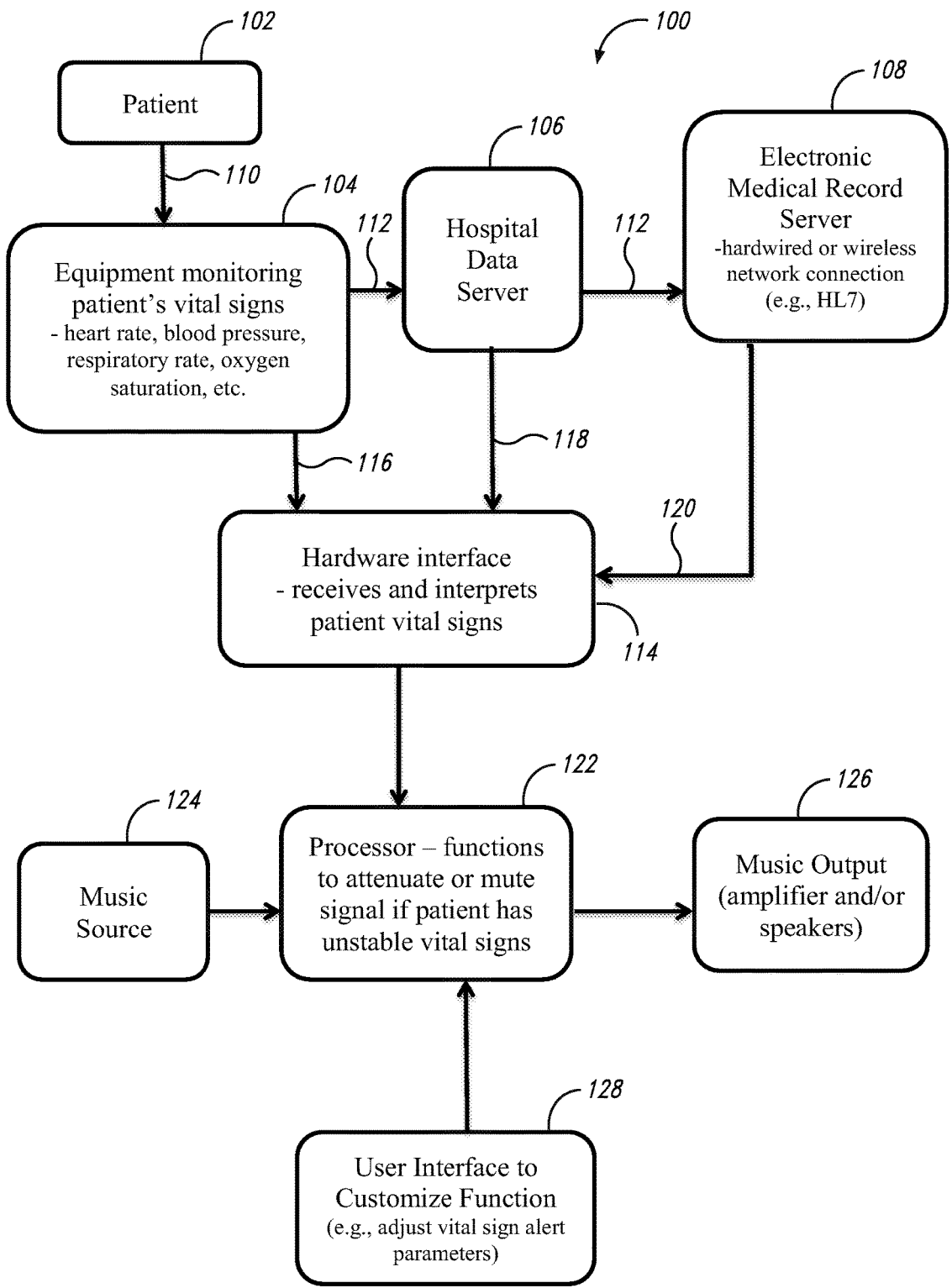
FIG. 1 is a flow chart showing the flow of patient information in a medical system and the interaction of patient information from operating room equipment with hardware for processing the information according to the instructions inserted by the user through the software interface of the present disclosure.

The unique, patient-centered sound system is designed for use in an operating room. FIG. 1 illustrates one representative implementation of the present disclosure wherein a system 100 for use with a patient 102 that is integrated with patient vital sign monitors 104 and may also be integrated with hospital networks 106 and electronic medical record solutions and servers 108. The patient 102 is connected by standard association means, such as sensors and cables or wireless devices 110, with medical equipment 104 for monitoring the patient's vital signs such as heart rate, blood pressure, respiratory rate, oxygen saturation, and other conditions. The information collected by the monitoring equipment 104 is relayed to the hospital data server 106, then to the patient's file in the electronic medical record (EMR) system 108 of the hospital or medical facility. This connection is typically accomplished by hardwiring 112 and the system should comply with the HL7 structure. The leader line from the monitoring equipment 104 to the EMR server 108 is also shown as interposed by the hospital data server 106, which connects to a hardware interface 114.

As illustrated in FIG. 1, three inputs 116, 118, 120 to the hardware interface 114 are from the monitoring equipment 104 directly, the hospital data server 106, and the EMR 108, respectively. In this way, data could arrive at the interface either pre- or post-EMR data transfer. Pre-EMR would obviate the need for logging into the EMR 108, selecting the patient, privacy concerns, etc. In some implementations, the same time that vital statistics are relayed to the EMR 108, the readings are also received by the hardware interface 114 to receive and interpret the data. The vital sign data may be received in many various file formats in order to be processed within the present disclosure's software application parameters. Alternatively, the vital signs can be relayed to the hardware interface 114 from the EMR. The preferred hardware component will not feed information back into the EMR or the vital signs monitor.

The hardware interface 114 is communicatively connected to a processor 122, which functions to rapidly decay or mute a music signal if the patient 102 is demonstrating unstable vital signs. The processor 122 receives a signal from a music source 124 and intervenes in the transmission of the music from the music source to a music output device 124, such as an amplifier or speakers or both. It is not transmitting an alarm in order to allow existing alarms from an anesthesia monitor (not shown) to be heard.

As described more fully below, a user interface 128 is communicatively coupled to the processor 122 and capable of allowing a user to adjust operating parameters of the system 100. The processor 122 may be any known computer, hardware CPU processors, and other known computing systems and devices. More generally, a "client" or "server" computing system or device may comprise any combination of hardware or firmware or combination thereof that can interact in the described manners, optionally when programmed or otherwise configured with particular software, including (without limitation) desktop or other computers, network devices, PDAs, cell phones, wireless phones, electronic organizers, Internet appliances, television-based systems, game consoles, media players and various other consumer products that include appropriate intercommunication capabilities. In addition, the functionality described may in some embodiments be provided via various modules, as noted above, or optionally may be separated into different (e.g., more or less) modules than are illustrated. The present disclosure may include a computer program stored on a medium to execute a method disclosed herein or may include a non-transitory computer-readable storage medium having a program to perform a method according to an implementation of the present disclosure stored thereon.

Figure 2:
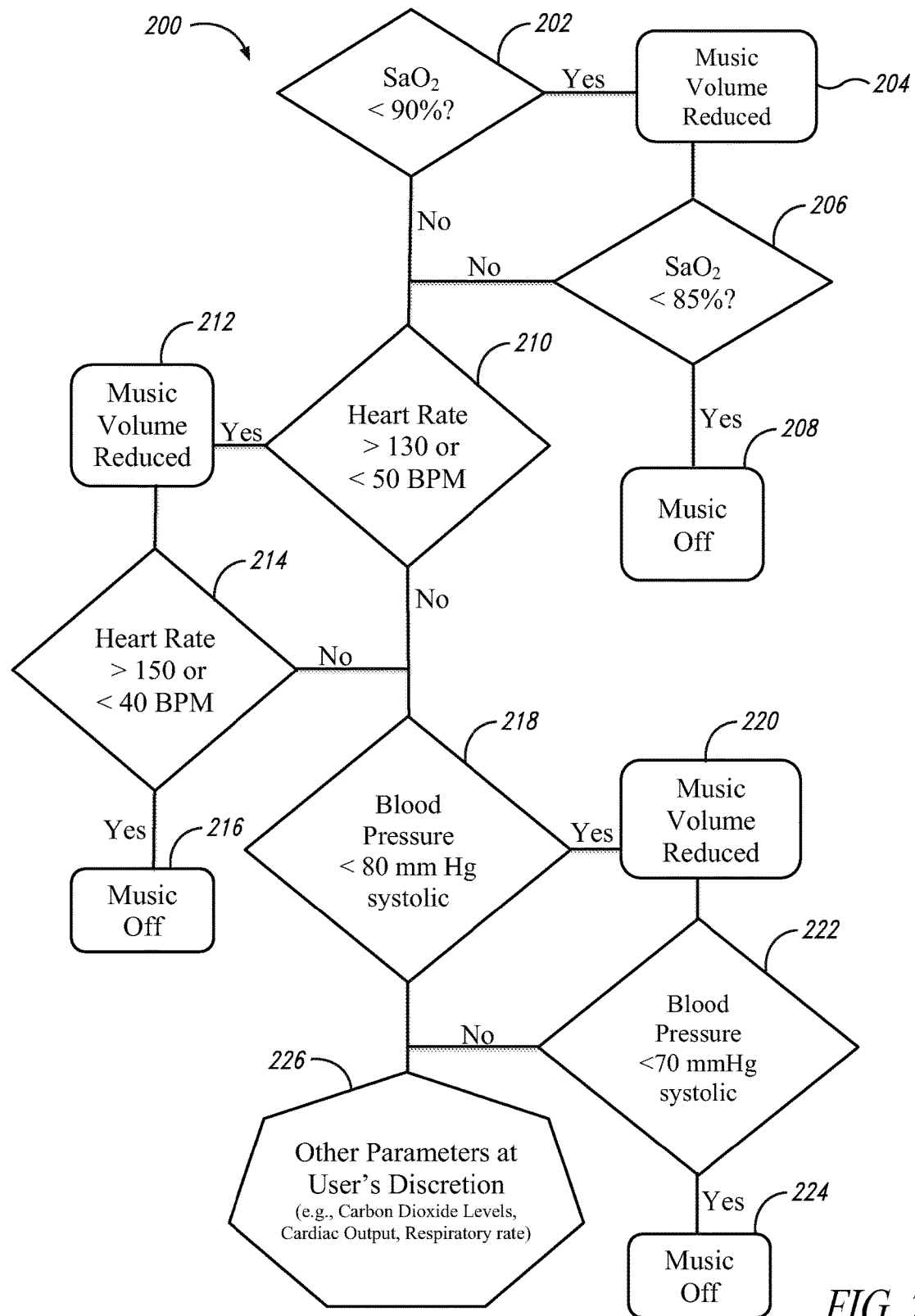
FIG. 2 is a logic tree diagram highlighting three common vital sign readings and medical parameters which may be desirably programmed into the present disclosure in order to control the music levels relative to changes in those vital signs.

Referring to the logic tree of FIG. 2, the central questions considered by the present disclosure is whether various vital sign indicators are within normal ranges, are on the brink of being worrisome, or have exceeded the risk thresholds that have been preset by the medical professionals. The "smart" operating room music device and system 100 of the present disclosure interfaces with or integrates a music system so that music will be silenced when a patient's vital signs are markedly abnormal. Although already being monitored by an anesthesia provider, the communication of emergencies through the operating room music system could provide an extra alert to other health care workers in the operating room who are attending to their own tasks.

The first query 202 shown in the flow chart 200 of FIG. 2 may be whether the oxygen saturation (labeled in FIG. 2 as SaO2) is below 90%. If not, no music volume intervention will be initiated (not shown). If the SaO2 drops below 90%, then the system 200 will decrease the audio system volume 204, and should the SaO2 continue to drop below 85% 206, then the system 200 will intervene to shut the music off 208 and either cut off the music input or activate the mute switch.

As a secondary vital sign for monitoring, the system 200 will reduce music volume or turn it off if the patient's heart rate does not fall within safe settings for that patient. In FIG. 2, decision box 210 indicates example heart rate settings for which concern may be raised, i.e., if the heart rate is below 50 beats per minute or greater than 130 beats per minute (BPM) the music volume will be reduced 212. Greater attention should be dictated when the heart rate falls within a preset critical zone, for example shown in decision box 214 as below 40 beats per minute or greater than 150 beats per minute (BPM). When the preset critical ranges are exceeded, the present disclosure will intervene to mute or shut off the music 216 to the operating room.

As a third example of a vital sign for monitoring, blood pressure, either by invasive or non-invasive measurements, can be monitored and set by the medical professional as it should be applied to each patient. When the monitoring device 104 indicates that the blood pressure has dropped below 80 millimeters of mercury in decision box 218, the music volume will be reduced 220 by the system. Should the patient's blood pressure exceed safe parameters and drop below 70 millimeters of mercury in decision box 222, for example, then the music would be cut off 224 to the speakers in the operating room. Perhaps a patient's SaO2, heart rate, or blood pressure are remaining consistent or are giving false readings, but other vital signs are fluctuating or dropping below a preset limit. In this case, the system 200 can be preset by the user 226 to indicate when those levels are exceeded by decaying or muting the volume. With the assistance of medical personnel, the system may provide an additional alert system that will prioritize, filter, and escalate its reaction based on any separate criteria or based on a combination of criteria with analytics and clinical decision support. An escalation in emergent circumstances results in further music filtering. In this implementation, the music must be manually turned back on if and when the operating room personnel deem it appropriate.

Ideally, a system processor is programmed to reduce the volume only in response to the patient condition signal being in the first range for a first period of time and muting the volume of the music source only in response to the patient condition signal being within the second range for a second period of time. In one implementation, the time periods are 60 seconds for the first range, adjustable in increments of 1 second up to 180 seconds, and 15 seconds for the second range, adjustable in increments of 1 second up to 60 seconds.

Figure 3:
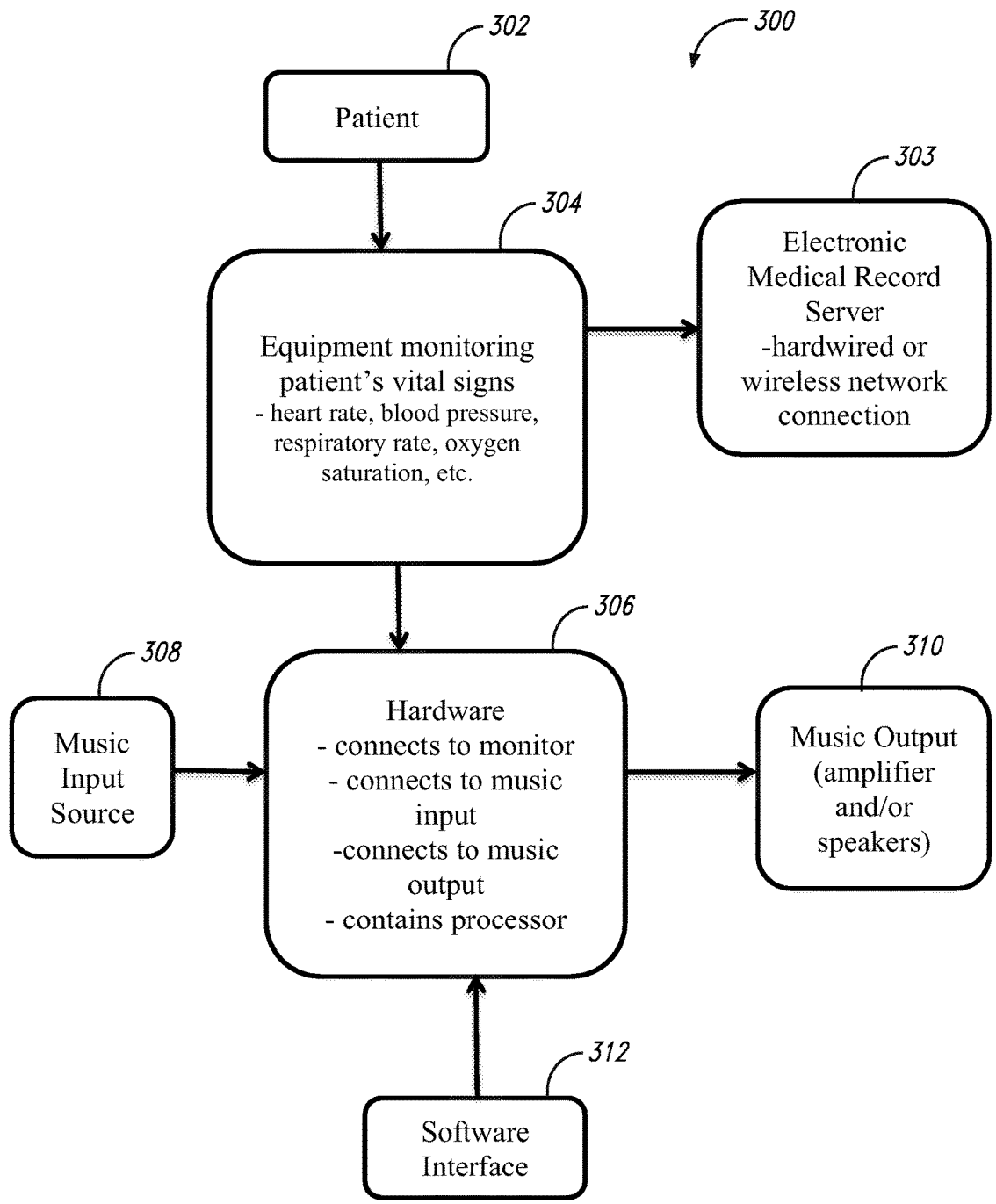
FIG. 3 is a flow chart showing the use of an off-the-shelf hardware unit with a software component according to the present disclosure receiving patient information from a medical monitoring system in order to control music levels according to the instructions inserted by the user through the software interface of the present disclosure.

In FIG. 3, the system 300 configuration is altered from that shown in FIG. 1 in which the monitoring equipment 304 or anesthesia monitor is connected to a patient 302, the EMR 303, and integrated with a music system via a software application interface installed on a piece of external, hard-wired hardware 306. Vital sign data is fed into the application software via an input to the hardware 306 from the anesthesia monitor or monitoring equipment 304. The music system includes a music input source 308 coupled to a second input of the hardware 306 and a music output device 310, such as an amplifier or speaker or combination thereof, coupled to an output of the hardware 306. The application software uses a set of parameters set by medical personnel via an interface device 312 coupled to another input to the hardware 306 to signal whether the patient 302 is becoming unstable.

As discussed in detail above, the parameters cover low oxygen saturation, abnormal blood pressure, etc. Abnormal vital signs cause volume output of the sounds system to be lowered or turned off. Although FIG. 3 illustrates a version of the software application that is not integrated with or coupled to the electronic medical record, such integration is possible as described in FIG. 1 and will be quite convenient when installed into off-the-shelf hardware that already contains medical record solution software and is fully integrated with the EMR system. An off-the-shelf piece of hardware may be a computer that has access to the Internet, in which case the music source may be internal to the hardware (not shown). The hardware may also cooperate with a docking station or Bluetooth® or wireless connection such that the music source may be connected to the hardware and accessed with the software application. The software application can be programmed to be used with any specific medical monitor model, individual device, or can be moved between unrelated medical monitors so long as the equipment has connectivity to the hardware with the installed software. In advanced anesthesia monitor models, the software application could be installed directly into the monitor's hardware and eliminate the need for connection to additional hardware (not shown).

Figure 4:
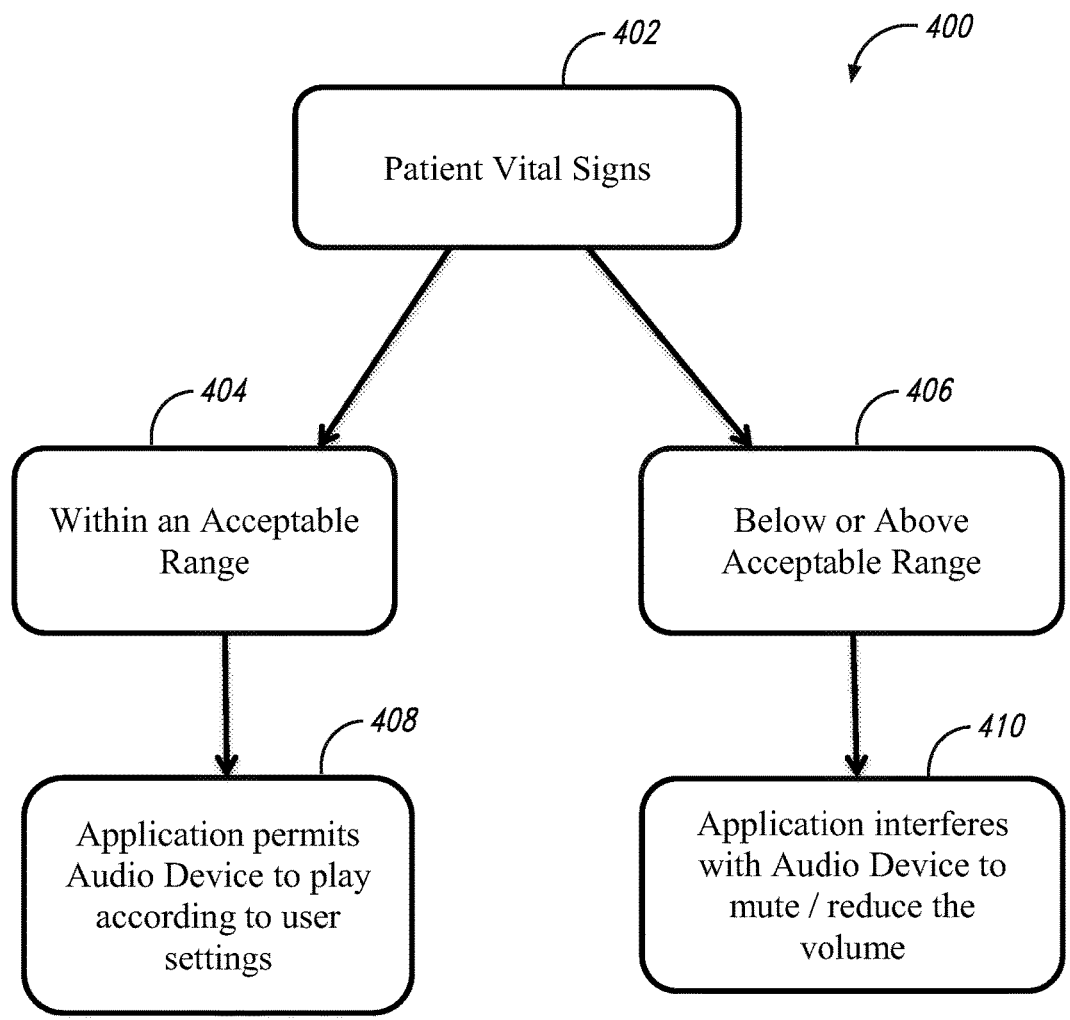
FIG. 4 is an isolated flow chart showing the reading of patient vital information and resulting action performed by the present disclosure.

As demonstrated in FIG. 4, the most basic controls implemented by the software application 400 are indicated. Patient vital signs 402 that are monitored are either within an acceptable range 404 or they are exceeding the limits of that range 406, which will result in a change to the audio device. Either the volume will be reduced 408 in the case of moderately abnormal vital signs, or the volume will be muted 410 when immediate attention is indicated by severely abnormal vital sign readings. In this case, the software application system 400 permits and facilitates a room-wide focus of the entire operating team on the safety of the patient.

Figure 5:
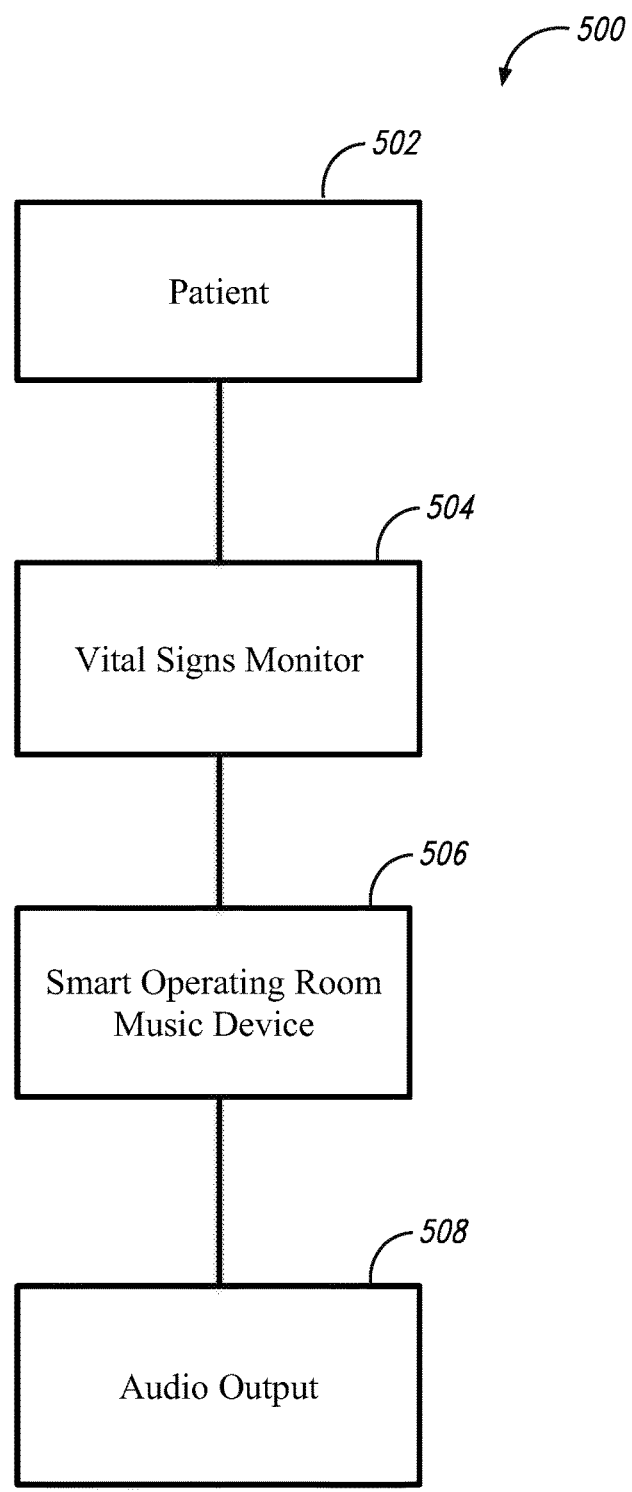
FIG. 5 is a diagram of the most basic, simplistic implementation of the present disclosure.
Figure 6:
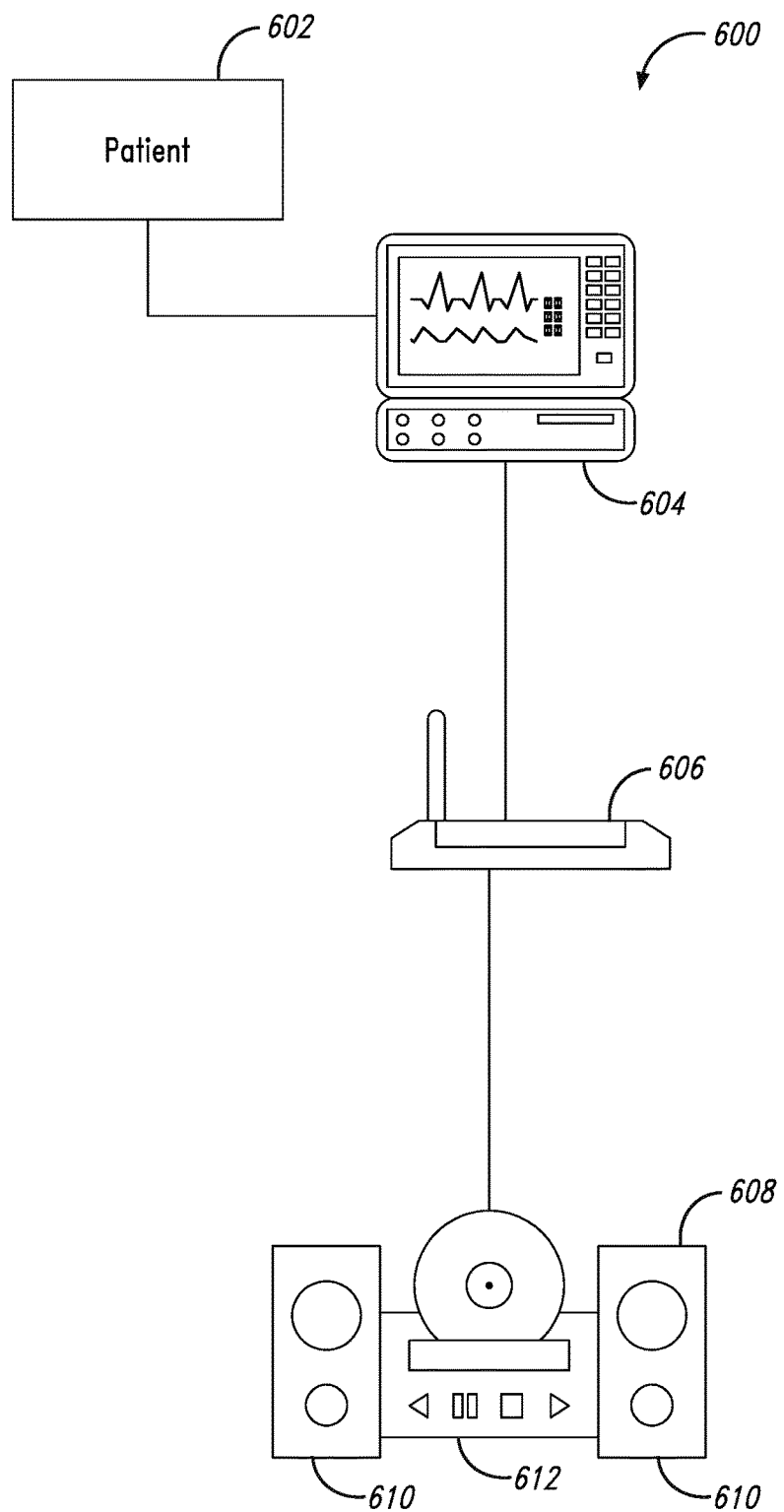
FIG. 6 is a schematic representation of some sample devices which could be employed to implement the present disclosure.

Referring to FIGS. 5 and 6, a system 500, 600 respectively of the present disclosure is demonstrated in its simplified form schematically (FIG. 5) and pictorially (FIG. 6) where a hardware device 506, 606 is the intermediary between the medical device monitoring system 504, 604 for the vital signs from the patient 502, 602, and the audio system output 508, 608 playing music into the background of the operating room. The audio output 508 will be the entire music system 608 in some instances, but will more commonly be simply a speaker system 610 that may have a built-in amplifier 612 or the amplifier may be integrated in the present system audio controls. Medical personnel will interact with each and every entity indicated in FIGS. 5 and 6. The patient's well being will dictate how the systems interact.

Though not shown, advanced implementations may exchange information between devices, meaning they have a multi-directional information flow, rather than a one direction information flow. For example, a button associated with the audio output may provide the means to pause the music playing via the smart music device 506, 606. The audio output may also send a signal to search for a Bluetooth® or wireless signal from the smart music device 506, 606. If the smart operating room music device 506, 606 is also networked with the EMR, it may exchange or provide information to the EMR or vital signs monitor via a local network connection. As shown pictorially in FIG. 6, the patient 602 is connected to a vital signs monitor 604 and the external device 606 of the present disclosure bridges and controls the music system 608 based upon the readings from the vital signs monitor 604.

Figure 7:
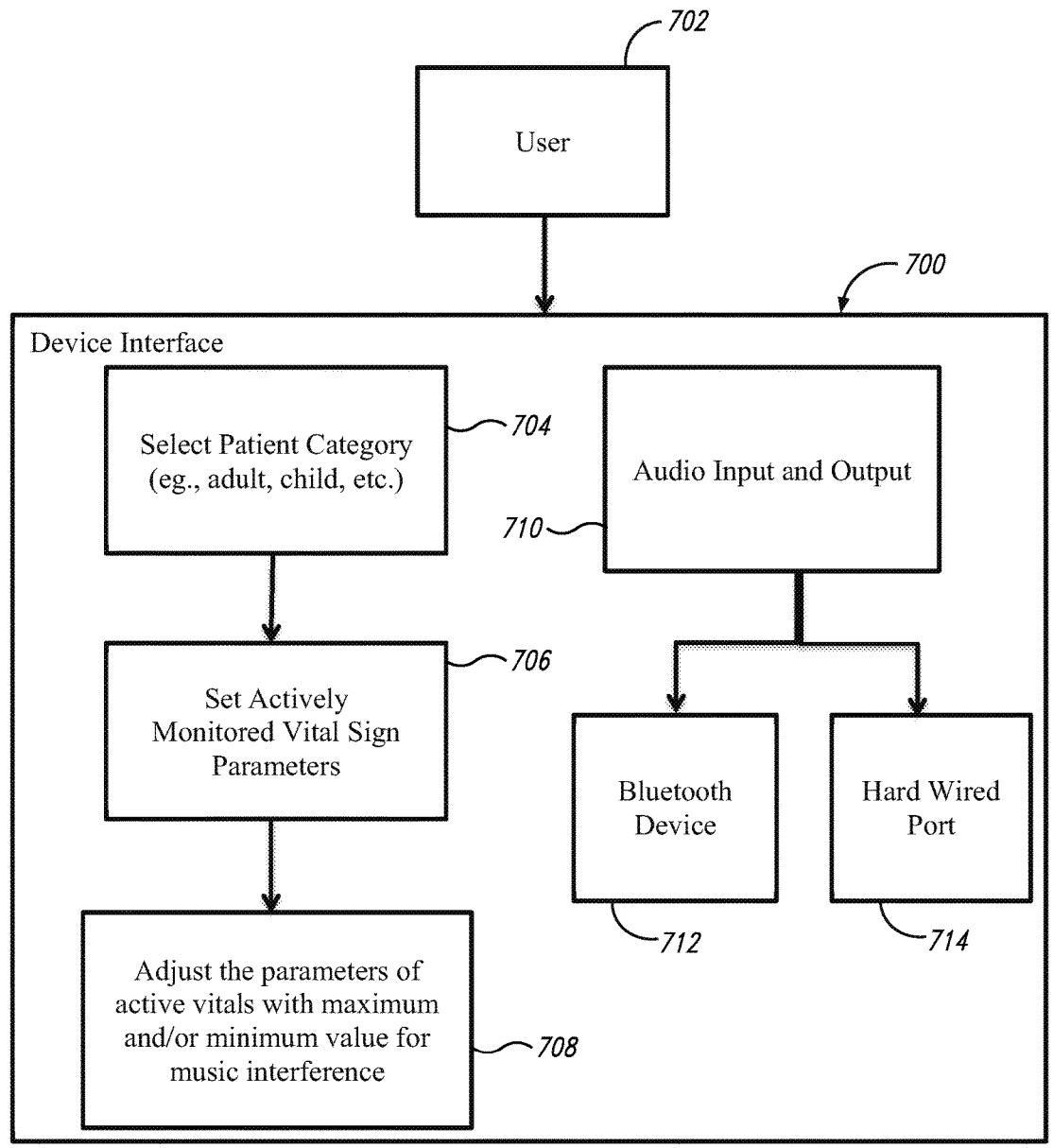
FIG. 7 illustrates the user interface of the present disclosure and some commands available to the user or multiple users.

The user's interaction with one implementation of the intelligent operating room music device 700 is illustrated in FIG. 7. A user 702, typically a member of the hospital staff, will pre-select general vital sign ranges that would be expected for a patient given their age, medical condition, and the nature of the surgical procedure. The vital sign parameter settings may optionally be adjusted by additional users, such as the anesthesiologist, at the outset of the surgical procedure. Music is often played using iPods or Pandora Radio and the anesthesiologist may or may not have control over what music is played and how loudly, but these settings will return some control to the doctors charged with monitoring the patient's vital signs. Based on the progress of the surgical procedure, excessive noise from instruments or conversation, and professional judgment, these parameters may be further modified with active adjustment options during surgery to result in a change to the maximum or minimum music interference in special circumstances.

The interface device 700 shown in FIG. 7 includes selection inputs for selecting the patient category 704, such as an adult or child, setting the actively monitored vital sign parameters 706, and adjustment of the active vital sign parameters 708 for minimum and maximum value, as well as the first and second periods of time discussed above. There is also a user interface for selection of audio input and output 710 and output to either a Bluetooth device 712 or a hard wired port 714.

With these controls, an anesthesiologist is able to exert more, active influence for the ambient noise in an operating room setting. For this particular implementation, where the music source is also integrated or controlled through the user interface, a user will manually set up the ambient or background music. Among selections available in the user interface will be afore-mentioned music input or audio source (iPod, Internet, CD, Bluetooth® device, etc.) 710 and audio output such as an existing hardwired port 714 or a Bluetooth® or wireless speaker 712.

Figure 8:
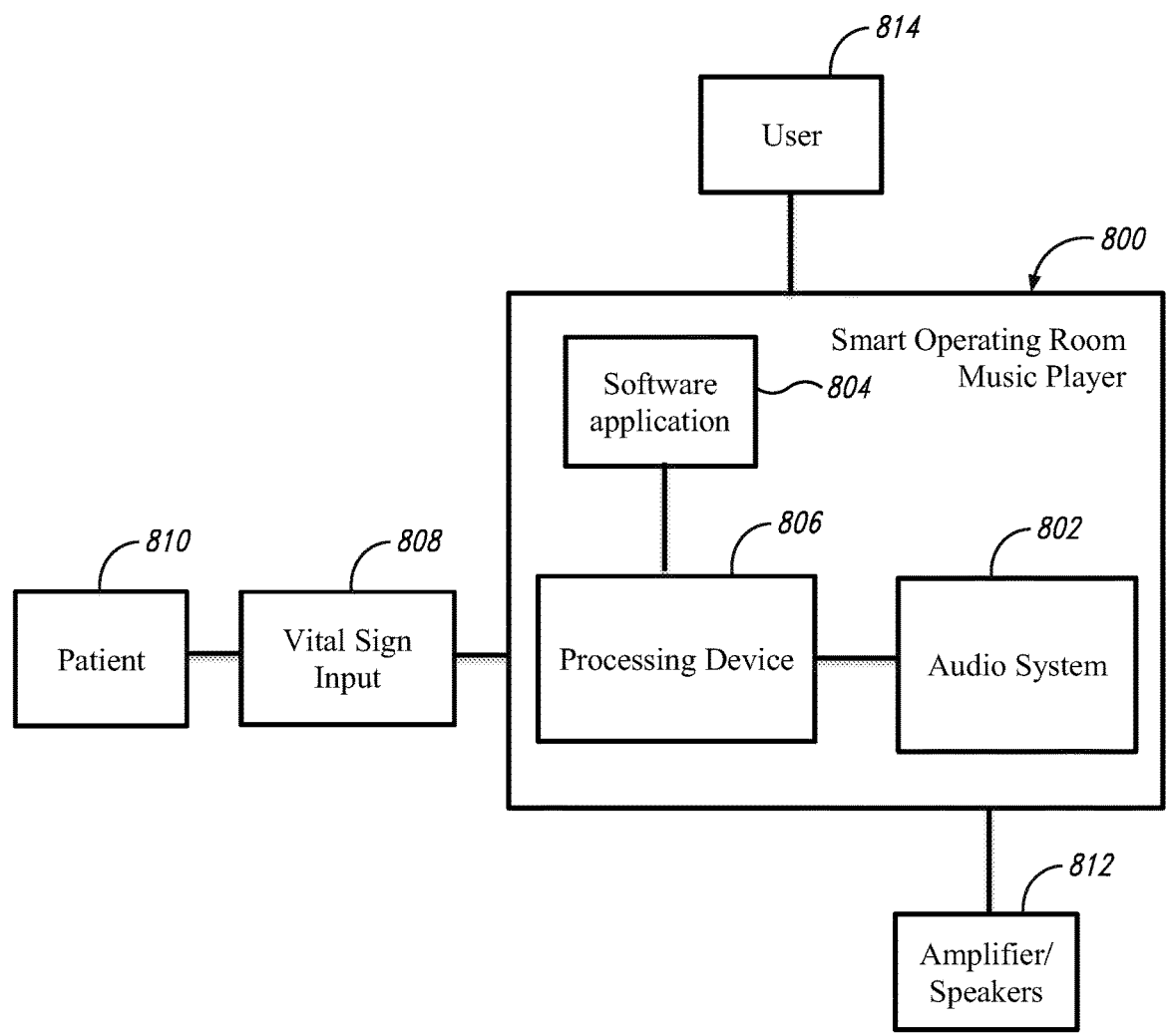
FIG. 8 is a diagram of an alternative implementation of the present disclosure.

An alternative implementation is illustrated in FIG. 8 where an intelligent, or smart operating room music player 800 houses the audio music system 802 and also has a software application 804 installed on board a processing device 806 so that the music system 802 only needs to be connected via a wired connection or wirelessly with a vital sign monitor or input system 808 associated with the patient 810. In advance models, vital signs may be relayed directly from the patient 810. The vital sign input system 808 may be from a standard stand-alone monitor such as an anesthesia monitor or they may be provided via another system such as through an EMR system. The smart operating room music system 800 will automatically mute or reduce the music volume to the music speakers or amplifier 812 when a patient's condition deteriorates, providing an additional element of safety in the operating room.

The muting of music will make the user 814 or health care professionals take notice and allow them to more easily register alarms from monitors. Although the music system could function as a stand-alone device, it is illustrated in FIG. 8 as having an external amplifier or speaker(s) 812. The amplifier could certainly be on board the smart operating room music player 800 (not shown) and only have output to an external speaker system that may be pre-installed in the operating room. The diagram in FIG. 8 indicates that the user 814 will continue to interact with the music system as feedback is given to the user. Two directional information flow is optional for the audio system to the processing device as well as from the vital signs input to the processing device. In certain circumstances, the speakers may have external controls allowing the music player to be paused, hence bidirectional communication is contemplated.

By way of example and not limitation, in this implementation as well as in other implementations, the smart sound system may be quite small. It may be about the size of a standard radio system such as that sized to fit in a car ranging in size from 3-4 inches high to 6-8 inches long and up to 10-12 inches wide. A plastic case will house electronic parts and provide ports for component cable inputs and outputs but may also have internal or external antennae for wireless capabilities.

Figure 9:
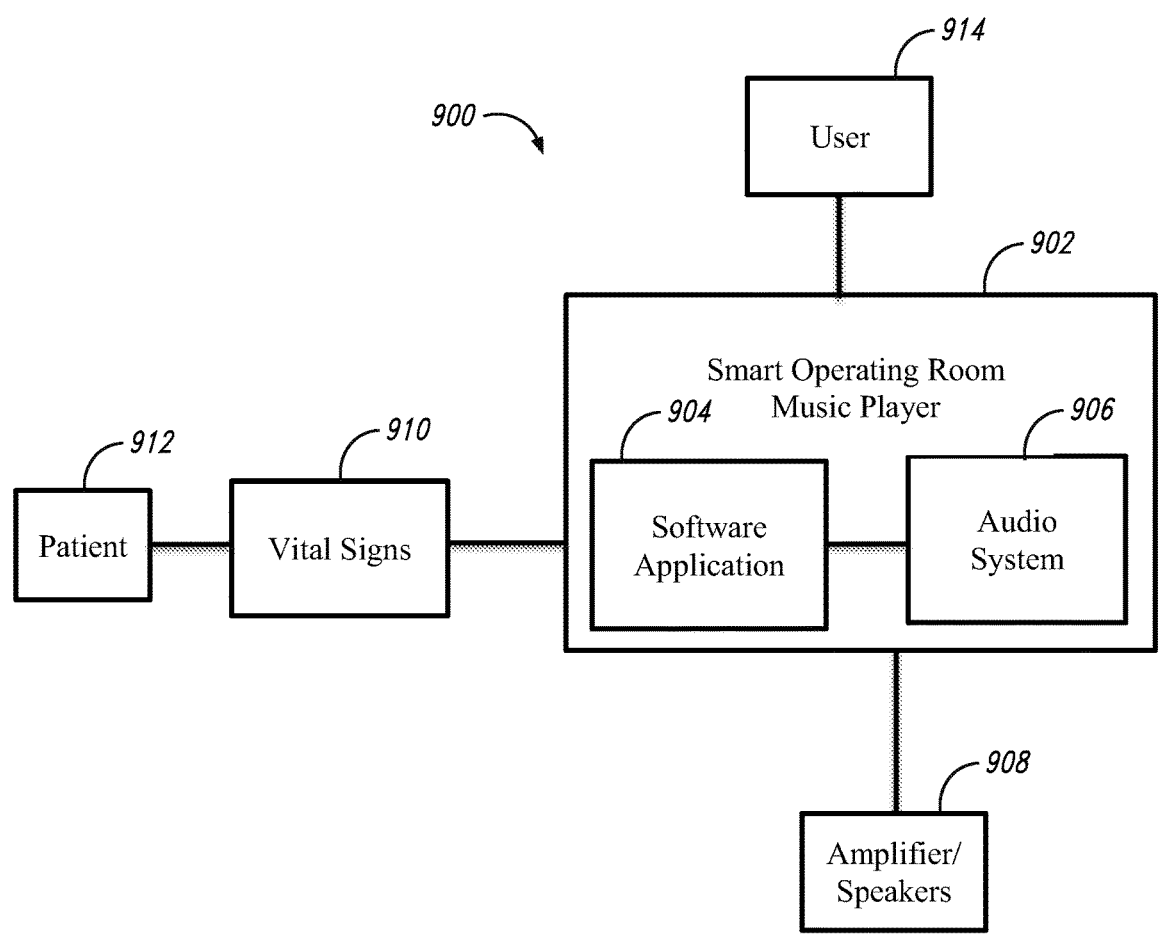
FIG. 9 is a diagram of a second alternative implementation of the present disclosure.

FIG. 9 illustrates another implementation of present disclosure in which the system 900 contemplates a device 902 having direct installation of a software application 904 (an App) on a mobile device such as a tablet, which also serves as the audio source or audio system 906 for the operating room so long as that device is receiving the vital sign readings from any source. By interaction of the software 904 with the audio source 906, music played via speakers 908 in the operating room may be controlled by vital signs 910 of a patient 912 via monitoring equipment as previously described. As this diagram illustrates, the operation of the system 900 is independent of any physical connection constraints, but can be entirely electronic in the right hospital framework, such as when a stand alone device could receive input of data either via hardwire (e.g., a RS232 Port) or wirelessly. Again, using the software user interface, medical personnel 914 will customized alarm settings (oxygen saturation level, blood pressure, heart rate, etc.) that lower the volume or completely mute the output of ambient music noise when thresholds are met or exceeded.

An external device added to an existing stereo system similar to an external Bluetooth® adapter could be added to nearly any existing stereo system in order to retrofit the present disclosure no matter how old, small, or compact an existing system may be. Facilities installing new systems may have the option to select the latest technologies which may require minimal software application installations to interface with other advanced products.

By way of example and not by way of limitation, examples of the range of rapid decay before complete muting of a music source should be planned to bring the decibels down from the average of about 87 dBA reading to about a 35 dBA and then to 0 dBA.

Though not illustrated, medical devices are often connected to the bridges and the PC platform using a medical device adapter (MDA). A single MDA connects to the serial port on the device and the USB port on the bridges or a PC. The bridging apparatus for use in an operating room according to the present disclosure may be used with more than one monitor. Thus, when the apparatus has more than one input, it may be programmed to receive information from more than one monitor from a single patient or more than one patient's monitor or more than one monitor from multiple patients so long as that bridge conveys outgoing commands to control an audio system. In certain applications, it may be useful to have more than one output to relay commands to more than one audio system. This will be accomplished by simply adding more output ports in wired settings or more channels for outgoing signals in wireless settings. The simplest bridge hardware component has at least one port to provide connectivity to an anesthesia monitor or similar medical monitoring device, even one that moves between patients.

Should more than one patient input be required, the bridge is connected to the monitoring device via a wired connection and travels with the device. The bridge optionally connects to a server via Ethernet or Wi-Fi connection (using the IEEE 802.11 a/b/g standard). The bridge can also be fixed within a room (e.g., mounted on the wall) and can provide connectivity to any bedside device. In hospital rooms such a device could be used to silence music when dictated by a medical situation.

An alternative to the single-port bridge for continuous standalone devices is the multiport bridge. This bridge, typically fixed within a room, can provide connectivity for any number of points of care (POC) devices simultaneously. Connectivity for eight devices will be sufficient in most cases. The devices connect to the bridge via a wired connection, while the bridge communicates with a facility or third party server either via a LAN connection or wirelessly (using the IEEE 802.11 a/b/g standard) through the hospital network. The multiport bridge may include in its user interface a menu to identify a patient and show the connectivity status of the devices. Based on hospital preference at the time of installation, the bridge can be configured to receive a personnel database feed and record the IDs of clinicians accessing the bridge. Disassociation can occur either manually using the bridge's user interface or automatically when a device is disconnected from the bridge.

Depending on FDA application of regulations to the various implementations of the present disclosure, each may be designated as a Class I or a Class II medical device. The device may be registered with FDA as a Class I medical device data system (MDDS). However, because certain implementations include notification functionality that allows users to set limits for physiologic parameters within the device software and to send notifications to clinicians in the form of silenced music if any of the parameters violate the preset limits, it may not qualify for Class I registration. This is because, according to the documentation issued by FDA to accompany its MDDS regulation (which can be viewed at http://edocket.access.gpo.gov/2011/pdf/2011-3321.pdf), "A device data system that facilitates clinical assessments or monitoring, such as alarm or alert functionality . . . is not an MDDS."

Class I includes devices that present the lowest risk and that, for the most part, do not require FDA clearance before being marketed. If the present disclosure can qualify as a MDDS, it may be able to avoid a 510(k) submission and registration as a Class II medical device. Based on a risk assessment of MDDSs, the FDA has determined that applying general Class I controls (such as those imposed by the Quality System Regulation) to the design and development of these devices would provide sufficient regulatory control to mitigate any associated risks. In simple terms, MDDSs are devices (including software-only systems) that transfer, store, or display medical device data and/or that convert medical device data formats within preset specifications, without controlling or altering the function or parameters of any connected medical device.

An MDDS cannot modify medical device data or the way it is displayed, nor can it be used for active patient monitoring. According to FDA, in some circumstances a device whose use may necessitate immediate clinical action is considered as providing active patient monitoring. This means that any system that provides alarm or alert functionality to notify clinicians of changes in a patient's condition is not an MDDS and must apply for Class II status. However, an MDDS can have alarms related to its own operational status and can transfer alarms generated by the medical device. The transfer of medical device alarms (e.g., for documentation purposes) is allowed if the alarm information remains in the same format after the transfer and is not used for active patient monitoring. To be classified as an MDDS, the system must not analyze or attempt to assign significance to alarm data being transferred. In at least one implementation of the present disclosure, an alarm is simply being transferred without analysis or assignment of significance. In the preferred implementation, interpretation, analysis, and assignment of significance will be desirable as the information is tied to the volume permitted for the ambient music levels. If this implementation does not meet the requirements for an MDDS (e.g., systems for communicating alarms as part of active patient monitoring), it will likely need to be registered with FDA as Class II medical devices, which require a 510(k) submission.

While the present disclosure is patient-centric, it may not require patient association for most implementations. The data parameters being supplied by medical professionals may be supplied even while maintaining patient anonymity. For at least some variations of the device, data will not be retained or stored and the alarms will not be tracked in the EMR. However, if the device is interfacing with the EMR or is exchanging data via a terminal hooked to the hospital servers, then patient association, also called patient context may be added by at least interconnectivity if not independent association.

By way of example and not by way of limitation, examples of connectivity and interactivity are discussed herein. The preferred device is meant to be used in a fixed location, such as a single surgical operating room. A fixed location will make a hardwired connection convenient and a hardwired connection which will increase speed and reliability of data transfer and response of the present disclosure. Hardwired connection will require device specific cable and device specific cables may complicate connectivity options. Alternative implementations will allow wireless communication between components of the present disclosure. Convenience in connectivity, sterility, and mobility will need to be weighed against speed and reliability of consistent communication. Device enhancements such as LED indicator lights may be incorporated to assist with visual cues of signal strength or device connectivity. Even cable-specific LEDs can provide an indication of the connectivity status. For example, green may indicate good connectivity and red may signal no connectivity. Additionally, the device solution can be configured to provide a visual indication of the connectivity status within the software application.

Some implementations of the present disclosure will provide software-only solutions that can be installed on any off-the-shelf PC hardware (e.g., existing PCs, tablets, or workstations) and provides connectivity to medical monitoring devices. The integrated music and alarm system may be applied to episodic monitoring devices as well as static or semi-static medical monitors. Hardware can be provided by the hospital or with the device in the form of a tablet.

The PC platform is attached to the medical device via a wired connection and is transported along with it (so that a single PC platform is connected to each medical device). The hardware communicates with a server wirelessly (using the IEEE 802.11 a/b/g standard) via the hospital network. The PC platform is provided by the hospital and connects to the medical device via the vendor-supplied cables so that each component travels with a single device. The hardware may be configured to communicate with the server via the hospital network by wired or wireless connection.

For anesthesia monitors, the software is loaded either onto an existing PC fixed within the room or onto a new, compact device that can be either fixed within a room or attached to the medical device. Either device must have a user interface so that the user may interact with the software. Vendor-supplied cables will again be used. When the PC is fixed within the room, multiple devices can be connected to it via its USB or other ports. For devices that move between patients (e.g., ventilators), the hardware, usually the supplied external hardware, can be permanently attached to the device so that it travels with the device and communicates with the server. In such cases, patient association can be patient-centric or location-centric and can be accomplished by any known methods such as those described herein.

An alternative implementation could permit a design using a device such as a compact fan-less PC. A compact PC is conveniently either fixed within a room or attached to the medical monitor. Such as device is desirable because it is a low-cost PC with no integrated screen or display. Because a user interface is desired, when a compact PC is used for medical device connectivity, a clinical workstation may be required at or near the point of care (POC) when the patient is first connected to the device. This is needed because a compact fan-less PC does not have a user interface, and it is recommended that the user access the EMR or the software application at the POC (via a clinical workstation) to ensure accurate association. The clinical workstation may be as simple as a tablet or personal computing device. Disassociation of the patient can occur automatically when the patient is discharged from or transferred within the hospital's Admit/Discharge/Transfer (ADT) system. Disassociation can also be done manually via the EMR (either using the system's native capability or through an embedded software functionality).

For non-networked devices, the solution software is used at the POC and can be installed on any off-the-shelf PC hardware (any existing iPods, PCs, tablets, or mobile workstations). The PC platform is typically provided by the hospital, but can also be provided by another vendor. The devices are connected to the PC hardware's serial or USB ports using off-the-shelf serial cables and serial-to-USB converters. The solution also supports a wireless Bluetooth® link between the medical device and the PC platform. The software communicates with the server via the hospital network, and provides notifications by altering music feeds. Since the PC hardware is provided by the hospital, a variety of connection options can exist between the medical device and the PC, including serial, Bluetooth®, IRDA (infrared), and Ethernet, depending on the individual capabilities of the medical device and of the PC hardware.

For continuous measurements, the software can be set up to collect multiple measurements from each device connected to it at selected intervals (e.g., once per second, once every 15 seconds, 15 times per minute, once per minute, etc.).

Figure 10:
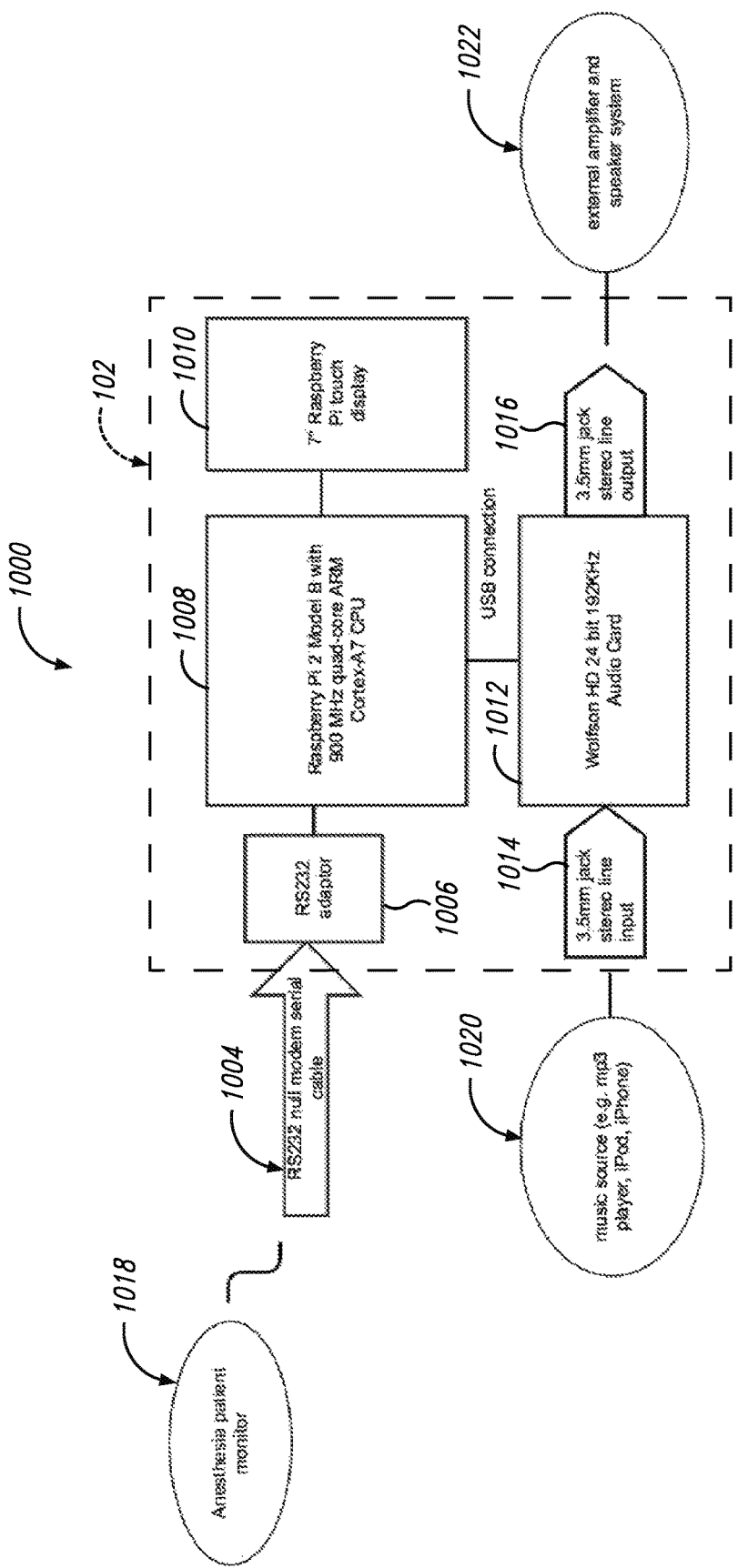
FIG. 10 is a diagram illustrating a representative preferred implementation of the present disclosure.

In a preferred implementation, shown by way of example in FIG. 10 and not by way of limitation, a system 1000 is shown have a self-contained portable device 1002 with a patient interface cable 1004, such as a serial null modem or RJ45 to DB9, that is coupled to the device 1002 via an RS232 Adaptor 1006. The device ideally contains an ARM processor 1008, such as a 900 MHz quad-core ARM Cortex-A7 CPU, RAM and flash memory, a color display 1010 with touch sensitivity, appropriate internal couplings, and a soundcard 1012 such as the Wolfson USB audio card with standard 3.5 mm audio connections 1014, 1016. The anesthesia patient monitor 1018 is coupled to the RS 232 Adaptor 1006 via the cable 2004, the music source 1020 is coupled to the line input 1014, and an external amplifier and speaker system 1022 is coupled to the line output 1016.

Those of ordinary skill in the art will recognize that the hardware components may be altered, replaced or augmented without deviating from the scope of the disclosure. Software components ideally include a Linux operating system, a graphic user interface (GUI), such as found in Qt libraries, a range fuzzy logic controller (RFLC) to set ranges and tolerances, an aggregator for polling patient condition signals and routing data to the RFLC, an audio mixer controller, medical device interface communication protocols and threads, and a watchdog timer to check for responsiveness and restart the device if necessary. Those of ordinary skill in the art will recognize the software components may be changed or altered without deviating from the scope of the disclosure.

Particular implementations of the present disclosure do not use a separate user interface for patient association. In at least those instances, patient association and disassociation, should they be needed, can occur in various ways including but not limited to:

(1) Using the medical monitor interface if the medical monitor allows entry of patient IDs, the solution can recognize and use this ID to tag the device data. Disassociation occurs when the patient is discharged from the monitor or when a new patient is admitted to the monitor. These systems may be automated with items such as scanners, or they may require manual entry.

(2) Through the EMR. Some EMRs have functionality to allow patient-device association and disassociation, and the present solution allows hospitals to use this native EMR functionality to associate and disassociate the patient. (For example, some EMR vendors may provide their own unique IDs and/or tags for the medical devices, and patient association occurs via the EMR using these IDs or tags.)

(3) Using the present software application. This application can be embedded into the EMR or used on its own, such as in a Web application. When it is embedded into the EMR, the clinician works within this application (e.g., a dedicated tab within the EMR) to associate the patient to the medical device (e.g., using supplied unique device IDs) and record the data.

(4) If the device is fixed within a room, patient association may optionally follow a location-centric approach, and disassociation can occur automatically when the patient is discharged from or transferred within the hospital's ADT system or when the monitor is disconnected from the device.

No information is preferably stored on the external bridge device. However, the multiport bridge will have an internal hard drive option to allow use of a standard 4 GB SD card. If configured, the device can store up to three days' worth of data and can be replaced with a higher-capacity card if needed. In the case of such a configuration, the data is automatically forwarded to the server once a network connection is detected. When the device software is used in a hospital working environment that requires user log-in, user authentication may not be possible during network downtimes (e.g., due to absence of a data feed from the personnel database), and users may have to revert to using manual music controls. The device with a memory configuration will be programmed with synchronized time with the hospital's time server, thus ensuring that the time on the bridge and any utilized PC platform is the same as that of the hospital's network clock. Device and software upgrades will be communicated to the bridging device via secure, industry standard methodologies such as through Web applications accessed over the hospital network.

For wireless configurations, a battery power supply such may provide power to the bridging device. In preferred wired configurations, electrical power will be the preferred power source for the smart music system and the interface and be supplied via a power cord.

The present disclosure will alleviate problems with alarm fatigue because the change in the level of the volume of background music will assist in alerting the personnel senses to the important alarm. It will alleviate problems with inadvertently disabled alarms because the settings can be customized to designated ranges prior to the induction. A quiet pulse oximeter will be recognized by the medical personnel because at the times when the monitor needs to have attentive listening, the music will be at low enough level that it can be heard. The present disclosure will allow enjoyable, energizing, or relaxing music to be played more safely at audible levels, because the music will adjust itself at the appropriate times. The present disclosure may even provide present music start times so that it will not begin until the common loud times in the operating room have passed, meaning after induction and before emergence. The music decibel oscillation will cue members of the surgical team when it is maybe inappropriate to be talking in the operating room or when such conversations should be more focused. With these features, patient safety alarms will be highlighted and patient injury or death due to inattentiveness to alarms will be avoided.

It is further intended that any other implementations of the present disclosure which result from any changes in application or method of use or operation, method of manufacture, shape, size, or material which are not specified within the detailed written description or illustrations contained herein are yet considered apparent or obvious to one skilled in the art are within the scope of the present disclosure.

The invention claimed is:

1. A device that alerts medical operating room personnel and facilitates surgical team communication during intraoperative critical events, including intraoperative hypoxemic and intraoperative hypotensive events, by controlling volume of a music source in a surgical operating room in response to data generated by existing anesthesia monitoring equipment in the surgical operating room, the device comprising:

a first input to be coupled to the anesthesia monitoring equipment and structured to receive an anesthesia monitoring signal from the anesthesia monitoring equipment, the anesthesia monitoring signal consisting of data pertaining to intraoperative oxygenation and intraoperative perfusion of a patient;

an output to be coupled to the surgical operating room music source; and a signal processor coupled to the first input and to the output and structured to receive the anesthesia monitoring signal and to generate a music volume control signal on the output to adjust the volume of the surgical operating room music source in response to the anesthesia monitoring signal in which the volume is reduced but not muted in response to the anesthesia monitoring signal being in a first range and muting the volume of the music source in response to the anesthesia monitoring signal being within a second range to alert the surgical team in the surgical operating room and facilitate surgical team communication during the intraoperative hypoxemic or hypotensive critical events.

2. The device of claim 1 wherein the first range and the second range are mutually exclusive.

3. The device of claim 1 wherein the anesthesia monitoring signal is a level of intraoperative oxygen saturation ($SaO_2$) in the patient and the first range is less than 90% and greater than 85% and the second range is less than or equal to 85%.

4. The device of claim 1 wherein the anesthesia monitoring signal is an intraoperative heart rate of the patient and the first range is greater than 130 BPM and less than 150 Beats Per Minute (BPM) or less than 50 BPM and greater than 40 BPM and the second range is greater than or equal to 150 BPM or less than or equal to 40 BPM.

5. The device of claim 1 wherein the anesthesia monitoring signal is a level of intraoperative blood pressure of the patient and the first range is less than 80 mm Hg systolic and greater than 70 mm Hg systolic and the second range is less than or equal to 70 mm Hg systolic.

6. The device of claim 1 in which the anesthesia monitoring signal comprises oxygen saturation level, heart rate, and blood pressure of the patient, and for an intraoperative oxygen saturation ($SaO_2$) level in the patient the first range is less than 90% and greater than 85% and the second range is less than or equal to 85%, and for an intraoperative heart rate of the patient the first range is greater than 130 BPM and less than 150 BPM or less than 50 BPM and greater than 40 BPM and the second range is greater than or equal to 150 BPM or less than or equal to 40 BPM, and for an intraoperative blood pressure of the patient the first range is less than 80 mm Hg systolic and greater than 70 mm Hg systolic and the second range is less than or equal to 70 mm Hg systolic.

7. The device of claim 1 comprising a second input that is coupled to the surgical operating room music source and to the signal processor and configured to receive a music input signal from the surgical operating room music source, the signal processor structured to receive the music input signal from the second input and to generate a music output control signal on the output in response to the anesthesia monitoring signal and the surgical operating room music input signal.

8. The device of claim 1 comprising a user interface coupled to the signal processor and configured to enable a user to adjust the first range and the second range of the anesthesia monitoring signal and a level of the volume of the surgical operating room music source in response to the anesthesia monitoring signal being within the first range.

9. The device of claim 1 wherein the signal processor is capable of processing at least one from among the following intraoperative anesthesia monitoring signals: oxygen saturation, heart rate, blood pressure, respiratory rate, carbon dioxide, temperature, invasive arterial blood pressure, cardiac output, invasive pulmonary artery pressures, central venous pressures, and EEG bispectral index.

10. The device of claim 1 wherein the signal processor is capable of reducing the volume of the music source only in response to the anesthesia monitoring signal being in the first range for a first period of time and muting the volume of the music source only in response to the anesthesia monitoring signal being within the second range for a second period of time.

11. A system that alerts surgical operating room medical personnel and facilitates surgical team communication by controlling surgical operating room music volume on music speakers in response to anesthesia monitoring signals generated during intraoperative hypoxemic or intraoperative hypotensive events by anesthesia monitoring equipment in the surgical operating room, the system comprising:
  a surgical operating room music player that includes:
    a first input coupled to the anesthesia monitoring equipment and structured to receive the anesthesia monitoring signals from the anesthesia monitoring equipment that consist of live data pertaining to intraoperative oxygenation and intraoperative perfusion of a patient;
    an output coupled to the surgical operating room music speakers;
    an audio system having an input terminal, an output terminal coupled to the output of the surgical operating room music player, and structured to output an audio signal to the surgical operating room music speakers; and
    a signal processor having an input terminal coupled to the first input to receive the anesthesia monitoring signals and an output terminal coupled to the input terminal of the audio system, the signal processor structured to generate a music volume control signal on the output terminal to the audio system to adjust a volume level of the audio signal in response to the anesthesia monitoring signals in which the volume level of the audio signal is reduced but not muted in response to the anesthesia monitoring signals being within a first range and muting the volume level of the audio signal in response to the anesthesia monitoring signals being within a second range to alert the surgical team in the surgical operating room and facilitate surgical team communication during intraoperative hypoxemic or intraoperative hypotensive events.

12. The system of claim 11 wherein the first range and the second range are mutually exclusive.

13. The system of claim 11 wherein the first range of the anesthesia monitoring signals is an intraoperative oxygen saturation ($SaO_2$) level of less than 90% and greater than 85% and the second range is of less than or equal to 85%, and further is an intraoperative heart rate of the patient in which the first range is greater than 130 BPM and less than 150 BPM or less than 50 BPM and greater than 40 BPM and the second range is greater than or equal to 150 BPM or less than or equal to 40 BPM, and further is an intraoperative blood pressure of the patient in which the first range is less than 80 mm Hg systolic and greater than 70 mm Hg systolic and the second range is less than or equal to 70 mm Hg systolic.

14. The system of claim 11 comprising a second input to the surgical operating room music player that is coupled to the signal processor and further comprising a user interface coupled to the second input and configured to enable a user to generate user input signals that are received by the signal processor via the second input and to cause the signal processor to adjust the first range and the second range of the anesthesia monitoring signals and a level of the surgical operating room music volume in response to the anesthesia monitoring signal being within the first range.

15. The system of claim 14 wherein the signal processor comprises one or more non-transitory computer-readable storage media having embodied thereon computer-useable instructions which, when executed by a computing device, causes the signal processor to receive the anesthesia monitoring signals and the user input signals and to generate the surgical operating room music volume control signal in response thereto.

16. The system of claim 14 wherein the signal processor is capable of processing at least one from among the following intraoperative anesthesia monitoring signals: oxygen saturation, heart rate, blood pressure, respiratory rate, carbon dioxide, temperature, invasive arterial blood pressure, cardiac output, invasive pulmonary artery pressures, central venous pressures, and EEG bispectral index.

17. The system of claim 14 wherein the signal processor is capable of reducing the music volume in the surgical operating room only in response to the anesthesia monitoring signal being in the first range for a first period of time and muting the volume of the surgical operating room music source only in response to the anesthesia monitoring signal being within the second range for a second period of time.

* * * * *